United States Patent
Hardy et al.

(10) Patent No.: US 9,783,637 B2
(45) Date of Patent: Oct. 10, 2017

(54) DRUG DELIVERY USING ELECTROCHEMICALLY-TRIGGERED BIODEGRADABLE ELECTROACTIVE MATERIALS

(71) Applicant: UNIVERSITY OF FLORIDA RESEARCH FOUNDATION, INC., Gainesville, FL (US)

(72) Inventors: John Hardy, Gainesville, FL (US); Christine E. Schmidt, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/222,000

(22) Filed: Mar. 21, 2014

(65) Prior Publication Data

US 2015/0265712 A1 Sep. 24, 2015

(51) Int. Cl.
*A61K 47/34* (2017.01)
*C08G 69/00* (2006.01)
*A61K 31/573* (2006.01)
*A61K 31/00* (2006.01)
*A61K 41/00* (2006.01)
*A61K 47/48* (2006.01)
*C08G 73/02* (2006.01)
*C08L 65/00* (2006.01)
*C08L 67/04* (2006.01)
*A61L 27/54* (2006.01)

(52) U.S. Cl.
CPC .............. *C08G 69/00* (2013.01); *A61K 31/00* (2013.01); *A61K 31/573* (2013.01); *A61K 41/0042* (2013.01); *A61K 47/48192* (2013.01); *A61K 47/48215* (2013.01); *C08G 73/024* (2013.01); *C08G 73/0266* (2013.01); *C08G 73/0273* (2013.01); *A61L 27/54* (2013.01); *C08L 65/00* (2013.01); *C08L 67/04* (2013.01)

(58) Field of Classification Search
CPC .......... A61L 27/54; C08L 67/04; C08L 65/00; A61K 31/00; A61K 47/48215
See application file for complete search history.

(56) References Cited

U.S. PATENT DOCUMENTS

| | | |
|---|---|---|
| 6,696,575 B2 | 2/2004 | Schmidt et al. |
| 2008/0262105 A1 | 10/2008 | Ferruti et al. |
| 2009/0325296 A1* | 12/2009 | Arinzeh ............... A61L 27/16 435/396 |

OTHER PUBLICATIONS

USPTO structure search, Mar. 2014.*

Guo et al Enhanced Electrical Conductivity by Macromolecular Architecture: Hyperbranched Electroactive and Degradable Block Copolymers Based on Poly($\epsilon$-caprolactone) and Aniline Pentamer, Macromolecules 2010, 43, 4472-4480, Dec. 2010.*
Stevenson—The controlled release of dexamethasone phosphate from polyterthiophene-based conducting polymers, PhD Thesis, University of Wollonsong, Sep. 2010.*
Rivers et al., Adv. Funct. Mater. 2002, 12 (1), January, 33-37.
Chen et al., Chem. J. Chin. Univ. 2004, 25 (9), 1768-1770.
Huang et al., Biomaterials 28 (2007) 1741-1751.
Svirskis et al., Journal of Controlled Release 146 (2010) 6-15.
International Search Report; dated Jun. 25, 2015; USPTO (PCT); Application No. PCT/US20151021770; 11 pages.
Baolin Guo, Anna Finne-Wistrand, and Ann-Christine Albertsson; Molecular Architecture of Electroactive and Biodegradable Copolymers Composed of Polylactide and Carboxyl-Capped Aniline Trimer; Biomacromolecules 201 0, 11, 855-863; Department of Fibre and Polymer Technology, School of Chemical Science and Engineering, Royal Institute of Technology, SE-100 44, Stockholm, Sweden.
Lee Seong Wei, Wendy Wee, Julius Yong Fu Siong, Desy Fitrya Syamsumir; Characterization of Antimicrobial, Antioxidant, Anticancer Property and Chemical Composition of Michelia champaca Seed and Flower Extracts; Stamford Journal of Pharmaceutical Sciences; S. J. Pharm. Sci. 4(1): 19-24; 2011.
Stevenson, Grace, The controlled release of duamethasone from polyterthiophene-based conducting polymers, Doctor of Philo8{lphy thesis, University ofWollongong. School of Chemistry, University ofWollongong. 2010. http:/ /ro.uow.edu.au/theses/3287.
Lihong Huang, Xiuli Zhuang, Jun Hu, Le Lang, Peibiao Zhang, Yu Wang, Xuesi Chen, Yen Wei, and Xiabin Jingt; Synthesis of Biodegradable and Electroactive Multiblock Polylactide and Aniline Pentamer Copolymer for Tissue Engineering Applications; Biomacromolecules 2008, 9, 850-858; State Key Laboratory of Polymer Physics and Chemistry.
Lili Cui, Danming Chao, Xiaofeng Lu, Junfeng Zhang, Hui Mao, Yongxin Li and Ce Wang; Synthesis and properties of an electroactive alternating multi-block copolymer of poly( ethylene oxide) and oligo-aniline with high dielectric constant; (www.interscience.wiley.com) DOI 10.1 002/pi.2815; Published online in Wiley Interscience: Apr. 7, 2010.
P. Santhosh, A. Gopalan, T.Vasudevan, Kwang-Pill Lee; Preparation and Characterization of Conducting Poly(diphenylamine) Entrapped Polyurethane Network Electrolyte; Published online in Wiley InterScience (www.interscience.wiley.com); Received Mar. 28, 2005; accepted Sep. 26, 2005; DOI 10.1002/ app.23326.

* cited by examiner

*Primary Examiner* — Gregory Listvoyb
(74) *Attorney, Agent, or Firm* — Thomas Horstemeyer, LLP

(57) ABSTRACT

A biodegradable electroactive material can be doped with a drug and the drug can be delivered to a living subject by stimulating the material with an electrical potential. The material (in this case a polymer) has an electrochemically responsive oligoaniline block terminated with a carboxylic acid moiety and is linked to an alcohol-terminated diol by an ester bond. Advantageously, the diol is PEG-400, PEG-2000, PCL-530, or PCL-2000.

5 Claims, 7 Drawing Sheets

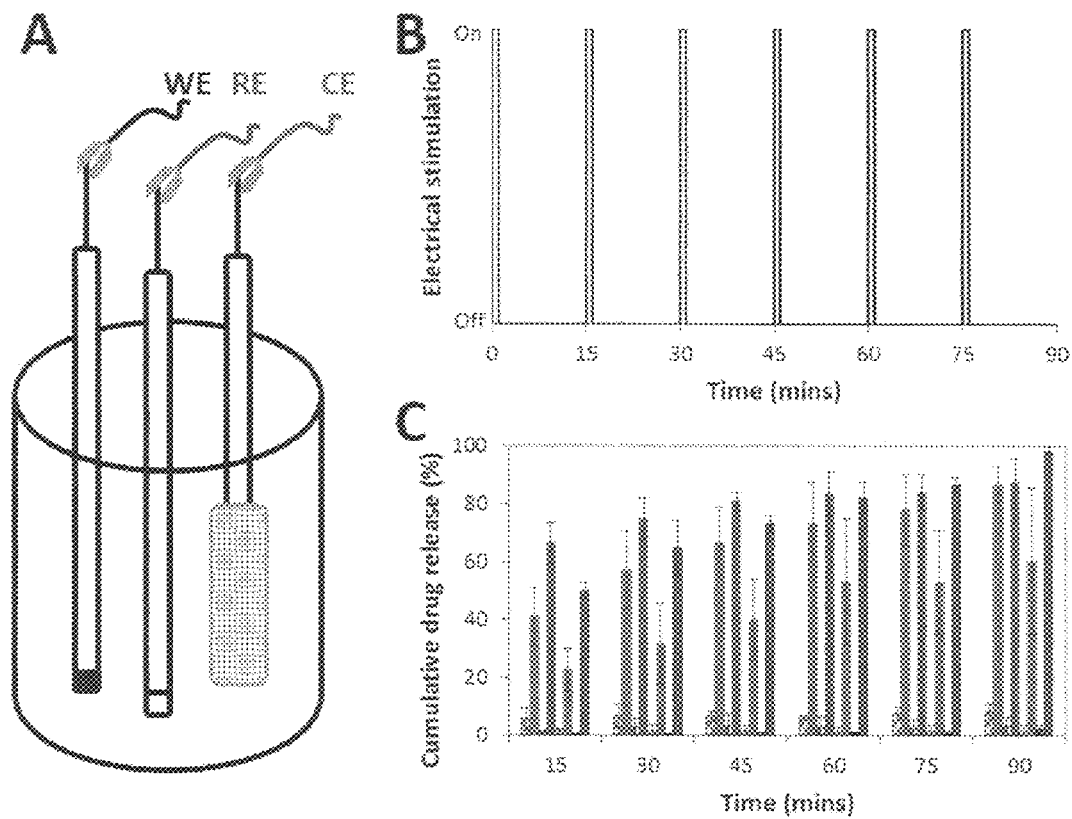
Figure 10. A) Experimental setup: Pt mesh counter electrode (CE), Ag/AgCl reference electrode (RE), DMP-doped polymer film coated on a glassy carbon working electrode (WE). B) Electrical stimulation paradigm. C) Release of DMP from films of 1-4 in PBS: with electrical stimulation (solid bars) or without electrical stimulation (checked bars). 1) red. 2) blue. 3) green. 4) purple.

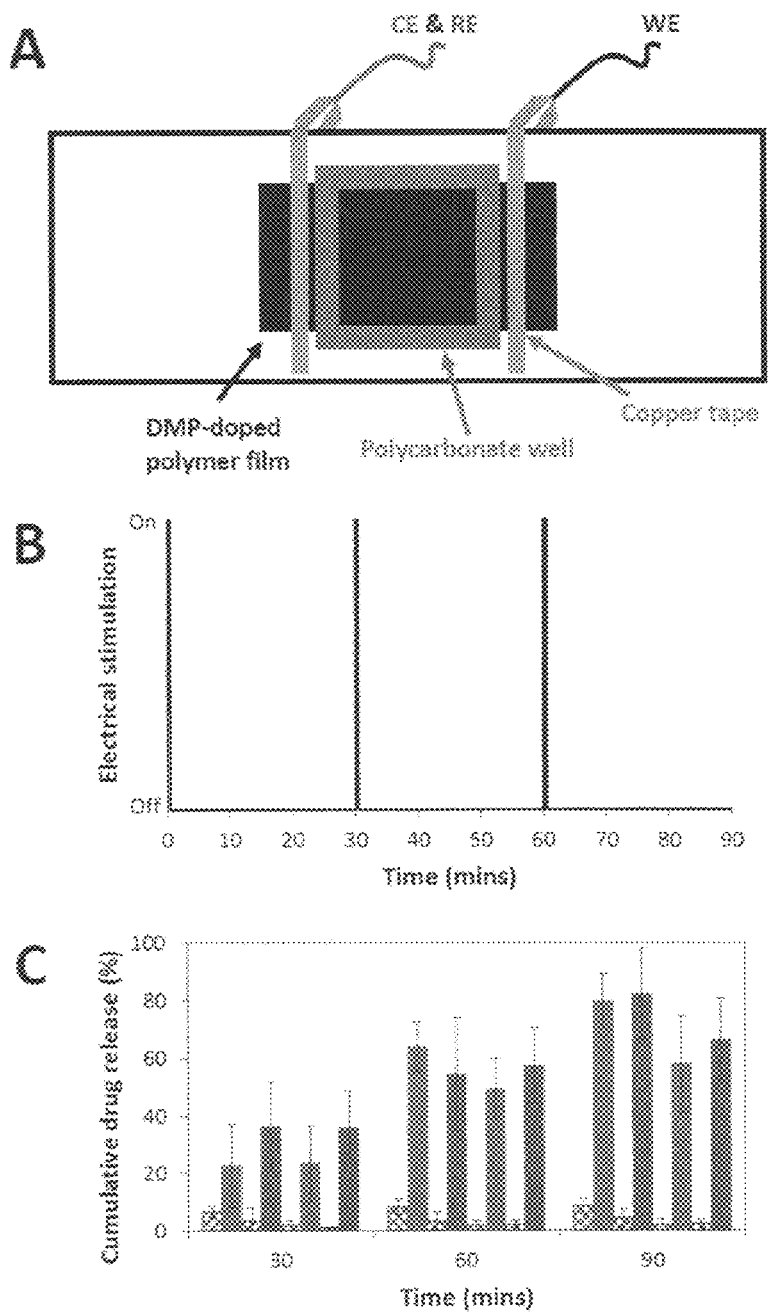
Figure 11. A) Experimental setup: counter electrode (CE), reference electrode (RE), working electrode (WE). B) Electrical stimulation paradigm. C) Release of DMP from films of 1-4 in PBS: with electrical stimulation (solid bars) or without electrical stimulation (checked bars). 1) red. 2) blue. 3) green. 4) purple.

DRUG DELIVERY USING ELECTROCHEMICALLY-TRIGGERED BIODEGRADABLE ELECTROACTIVE MATERIALS

BACKGROUND OF THE INVENTION

The invention relates to electroactive materials, and more particularly relates to biodegradable electroactive materials (some of which conduct electricity). In its most immediate sense, the invention relates to biodegradable electroactive materials that can be used for delivering drugs to living subjects.

Researchers have investigated the use of electroactive polymers as drug delivery agents. A literature review (D. Svirskis, J. Travas-Sejdic, A. Rodgers, S. Garg, *J. Control. Rel.* 2010, 146, 6) discusses delivery of adenosine triphosphate, dexamethasone phosphate, DNA, dopamine, nerve growth factor, and N-methylphenothiazine. However, the electroactive polymers used to deliver these drugs are not fully biodegradable. And, while some biodegradable electroactive polymers are known (T. J. Rivers, T. W. Hudson, C. E. Schmidt, *Adv. Funct. Mater.* 2002, 12, 33) they are unsuitable for use in drug delivery systems because they only become electroactive after being oxidized using iodine, and iodine is toxic.

It would be advantageous to provide a fully biodegradable electroactive material that could be used to deliver a drug to a living subject without requiring use of an oxidizer such as iodine.

SUMMARY OF THE INVENTION

In accordance with the invention, there are provided fully biodegradable electroactive materials from which drug delivery can be triggered electrochemically.

The invention proceeds from the realization that water soluble electrochemically responsive units (e.g., oligoanilines, oligothiophenes, polypyrrole, various monomers, ferrocene, porphyrin) are an essential characteristic for delivery of a drug to a living subject from fully degradable materials. By linking water-soluble electrochemically responsive units (particularly carboxylic acid-terminated oligoaniline blocks) to other units (particularly alcohol-terminated diols, including alcohol-terminated blocks of either polyethylene glycol (PEG) or polycaprolactone (PCL)) using biodegradable bonds, particularly ester bonds, biodegradable electroactive materials (particularly polymers) are formed. When electrochemically responsive units are "doped" with a drug, drug delivery can be triggered by application of an electrical potential. Furthermore, as long as the molecular weight of the units is smaller than the 70 kDa renal filtration threshold, the kidney can remove the degradation products of the inventive materials from the bloodstream.

In accordance with the invention, an electroactive material comprises a water soluble electrochemically responsive unit linked to another unit by a biodegradable bond, with the molecular weight of the units being smaller than the renal filtration threshold. Advantageously, the material is a polymer. Preferred embodiments of the invention are of the form

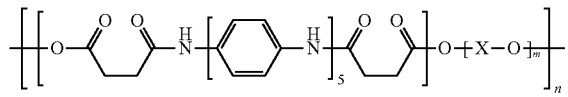

wherein X is polyethylene glycol (PEG) or polycaprolactone (PCL). Advantageously, and in accordance with the preferred embodiments, X is poly(ethylene glycol)s having average molecular weight of 400 Da. (PEG-400), poly (ethylene glycol)s having average molecular weight of 2000 Da. (PEG-2000), poly(caprolactone)s having average molecular weight of 530 Da. (PCL-530) or poly(caprolactone)s having average molecular weight of 2000 Da. (PCL-2000).

To deliver a drug to a living subject, in a method according to the invention an electroactive material in accordance with the invention is doped with the drug to be delivered and the doped material is stimulated by application of an electrical potential. Camphorsulfonic acid can be used as a dopant to promote the adhesion of C6 cells, keratinocytes, MC3T3-E1 cells, osteoblasts, PC12 cells, Schwann cells, human Mesenchymal stem cells, human dermal fibroblasts and potentially others. Dexamethasone phosphate can be used as a dopant in instances wherein the invention is used to deliver it to a living subject in order to utilize its anti-inflammatory properties.

BRIEF DESCRIPTION OF THE DRAWINGS

The invention will be better understood with reference to the following illustrative and non-limiting drawings, in which:

FIG. 10 schematically illustrates an experiment to measure delivery of dexamethasone phosphate in a context similar to use of an implant to stimulate the central nervous system wherein tissue surrounding the implant is used as a counter electrode;

FIG. 11 schematically illustrates an experiment to measure delivery of dexamethasone phosphate in a context similar to powering a conductive tissue scaffold.

DETAILED DESCRIPTION OF PREFERRED EMBODIMENTS

Preferred embodiments of the invention were produced by esterification of aniline pentamers terminated with carboxylic-acids. Production of the aniline pentamers will be discussed initially; synthesis of the preferred embodiments will be discussed afterward.

A. Production of Precursor Aniline Pentamers

Figure 1:
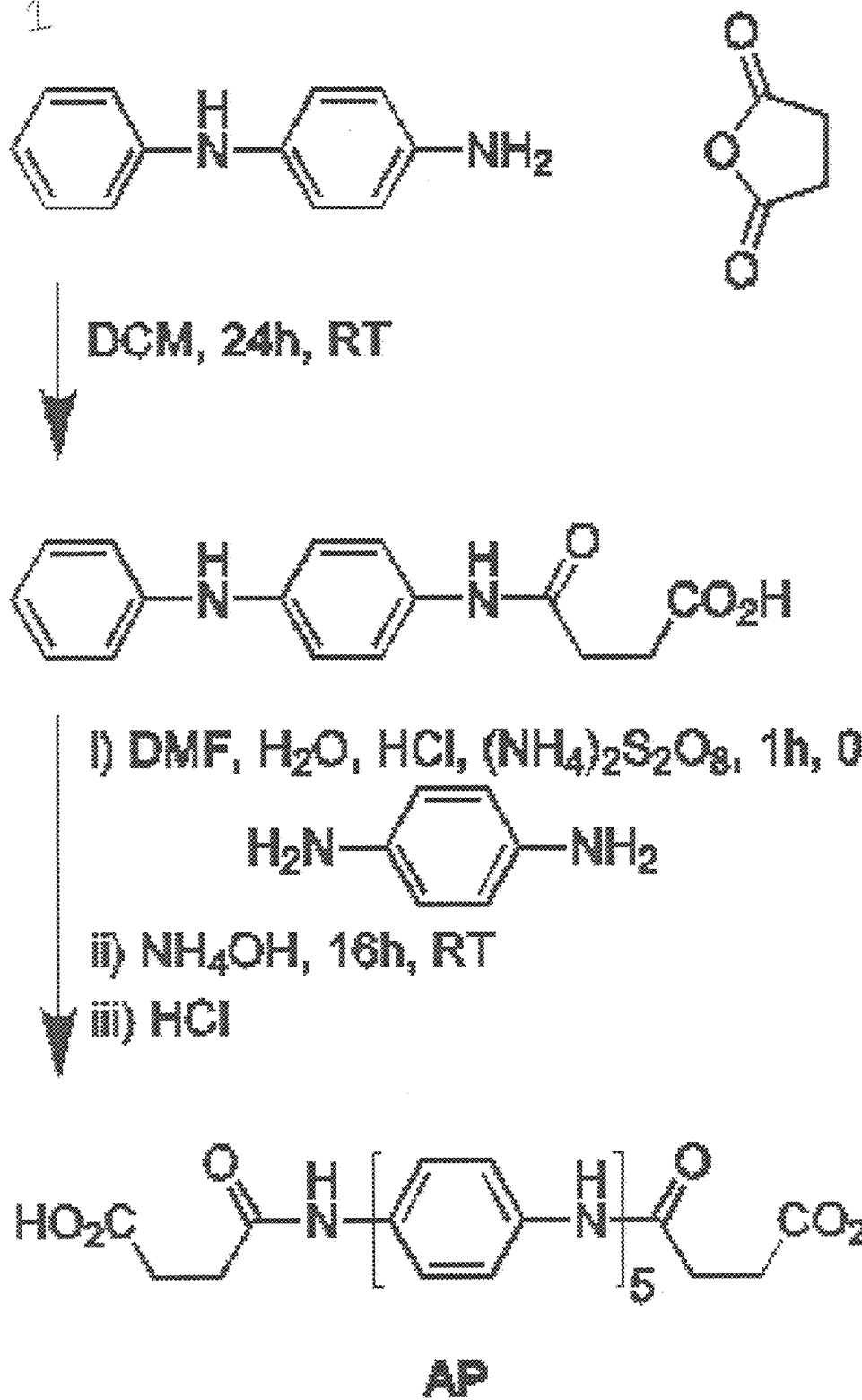
FIG. 1 shows the synthesis of carboxylic acid-terminated aniline pentamers used to synthesize the preferred embodiments of the invention.

Referring first to FIG. 1, the synthesis of the carboxylic acid-terminated aniline pentamers was adapted from a known method (L. Chen, Y. Yu, H. Mao, X. Lu, W. Zhang, Y. Wei, *Chem. J. Chin. Univ.* 2004, 25 (9), 1768-1770). N-phenyl-1,4-phenylenediamine (9.2 g, 50 mmol) and succinic anhydride (5.0 g, 50 mmol) were dissolved in dichloromethane (DCM, 300 mL) and stirred overnight at room temperature. The product was isolated by filtration, washed with diethyl ether until the diethyl ether was clear and colorless, and dried under vacuum for 24 hours, yielding 12.0 g (42 mmol, 84% yield) of blue-gray solid (a succinic acid-capped aniline dimer). This blue-gray solid (2.9 g, 10 mmol) and p-phenylenediamine (0.54 g, 5 mmol) were dissolved in dimethylformamide (DMF, 15 mL) and the solution cooled to 0° C. on ice. A cooled solution of DMF (30 mL), water (25 mL) and concentrated hydrochloric acid (5 mL) was added. A solution of ammonium persulfate (2.28 g, 10 mmol) in aqueous hydrochloric acid solution (50 mL, 1 M) was added slowly and the reaction mixture stirred quickly for 1 hour at 0° C. After this time the reaction mixture was added to water (300 mL) resulting in the precipitation of a solid, which was isolated by filtration. The product was reduced by stirring a suspension of the product in aqueous ammonia (300 mL, 1 M) overnight, after which the pH was lowered to 2-3 by addition of aqueous hydrochloric acid (1 M), and the product isolated by filtration. The product was dried under vacuum at 45° C. for 48 hours. A solution of the crude product (3.0 g) in DMF (15 mL) was slowly added to ethanol (150 mL) resulting in the precipitation of a solid material that was isolated by filtration and dried under vacuum. The product was purified by Soxhlet extraction with 1,2-dichloroethane followed by THF. The succinic acid-capped aniline pentamer (AP at the bottom of FIG. 1) was dried under vacuum for 48 hours, after which 1.8 g (2.7 mmol, 54% yield) was isolated in an analytically pure form in accordance with the literature.

B. General Methodology for Synthesizing the Preferred Embodiments

The preferred embodiments of the inventions described herein are all polymers, but it will be understood that this is only preferred and that materials in accordance with the invention need not be polymeric; diols need not necessarily be employed and other biodegradable bonds can be used to link to the water soluble electrochemically responsive units. The type of biodegradable bond employed will be determined by the type of blocks that are bonded together. Furthermore, it will be understood that although the preferred embodiments described herein use carboxylic acid-terminated oligoaniline blocks as the electrochemically responsive units, other water soluble electrochemically responsive units can be used instead. The herein-described preferred embodiments were produced by a synthesis adapted from a known method (L. Huang, J. Hu, L. Lang, X. Wang, P. Zhang, X. Jing, X. Wang, X. Chen, P. I. Lelkes, A. G. MacDiarmid, Y. Wei, *Biomaterials* 2007, 28, 1741). In short, alcohol-terminated poly(ethylene glycol)s or poly(caprolactone)s (3 mmol) were dissolved in N-methyl-2-pyrrolidone (NMP, 20 mL), to which was added AP (2.0 g, 3.0 mmol), dicyclohexylcarbodiimide (DCC, 1.9 g, 9.0 mmol) and 4-dimethylaminopyridine (DMAP, 0.2 g, 2.0 mmol). The reaction mixture was stirred at room temperature under an inert atmosphere of argon. After 72 hours the reaction mixture was filtered and added drop-wise to diethyl ether (1.5 L) that was stirred to assure the precipitation of a fine powder of the respective polymer. The stir bar was removed and the product was allowed to settle to the bottom of the container (typically 15-30 minutes). The diethyl ether was removed via pipette suction, and the polymer-rich layer at the bottom of the container was concentrated with a rotary evaporator to yield a thick oil. The oil was dissolved/dispersed in chloroform (10 mL), after which it was re-precipitated in diethyl ether, and this process of resuspension in chloroform followed by re-precipitation in diethyl ether was repeated two more times. The resulting polymers were dried under high vacuum for 24 hours. The polymers could be reduced to the leucoemeraldine state via brief exposure to aqueous hydrazine for ca. 15 minutes (after which no further gas was observed to evolve) followed by dialysis against ultrapure water in a cellulose dialysis tube with a molecular weight cutoff of ca. 3,500 Da, and dried under high vacuum for 48 hours.

C. Synthesis of the First Preferred Embodiment of the Invention

Figure 2:
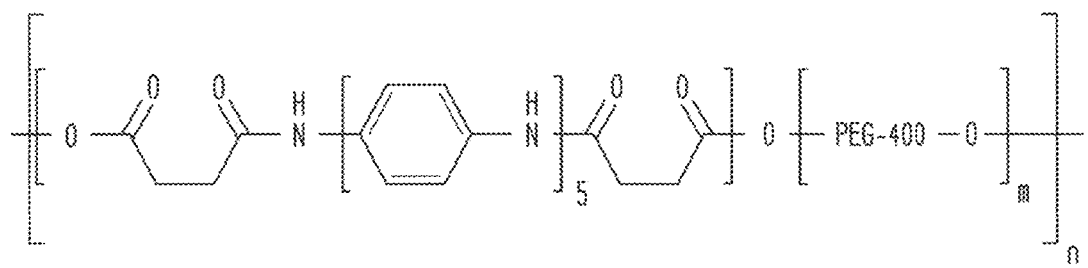
FIG. 2 shows the structure of a first preferred embodiment of the invention, using PEG-400.
Figure 3:
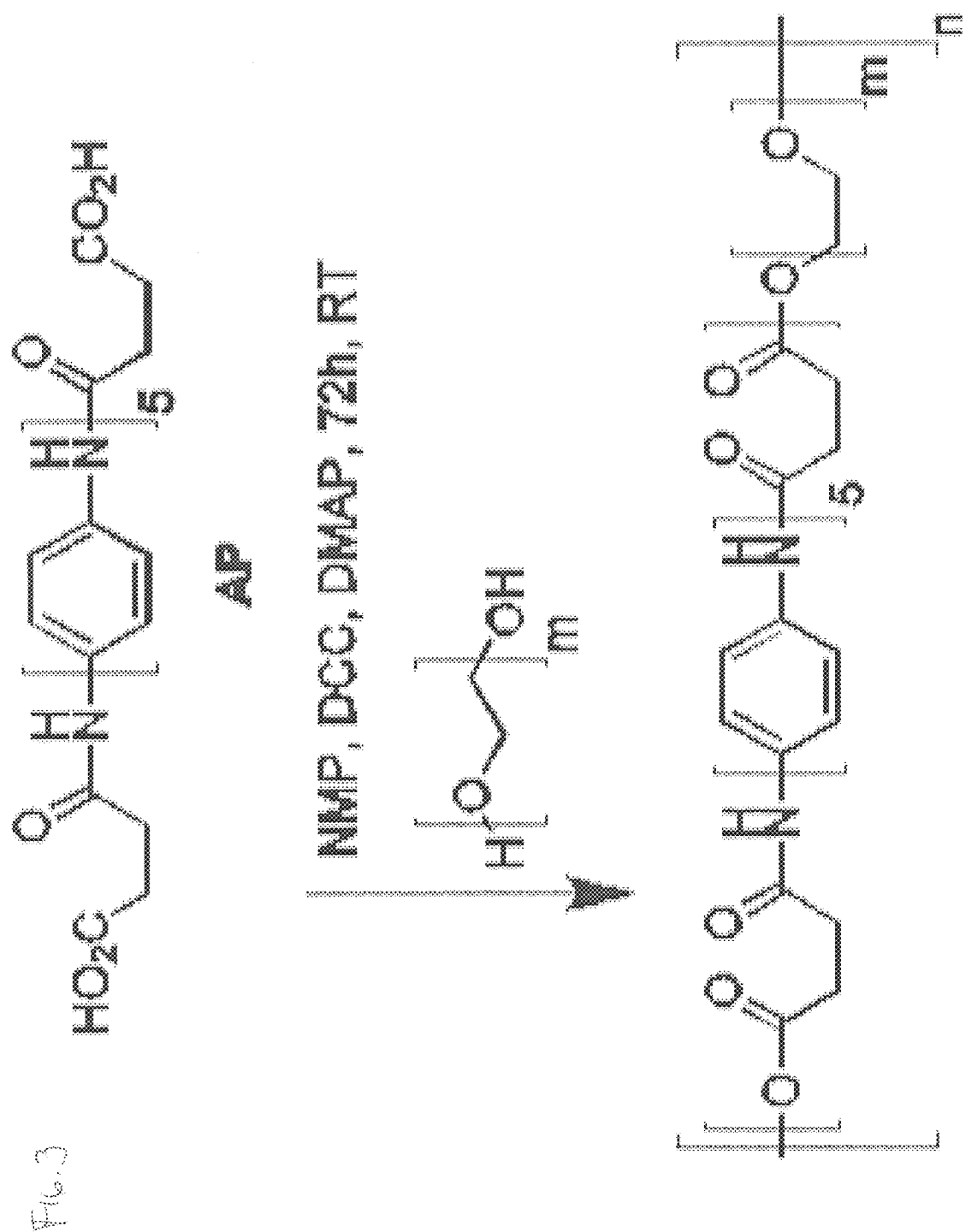
FIG. 3 shows the synthesis of the first and second preferred embodiments of the invention.

The first preferred embodiment of the invention (FIG. 2) was synthesized using poly(ethylene glycol) with an average molecular weight of 400 Da. The synthesis is shown in FIG. 3. 1.6 g of the first preferred embodiment was isolated via this procedure, in a yield of 50% by mass.

D. Synthesis of the Second Preferred Embodiment of the Invention

Figure 4:
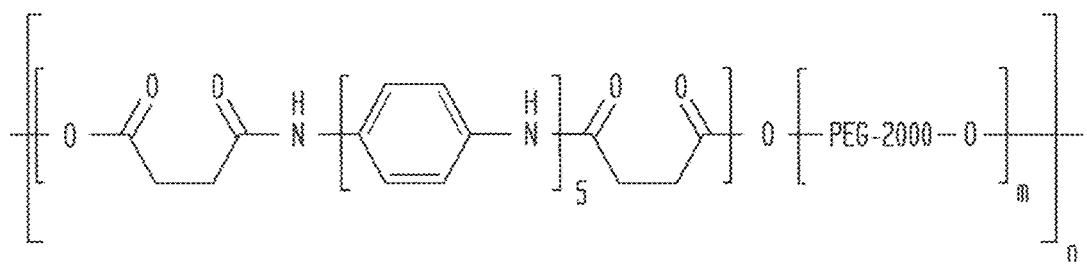
FIG. 4 shows the structure of a second preferred embodiment of the invention, using PEG-2000.

The second preferred embodiment of the invention (FIG. 4) was synthesized using the same synthesis as was used to produce the first preferred embodiment, except that using alcohol-terminated poly(ethylene glycol)s with an average molecular weight of 2,000 Da. were used. 4.25 g of the second preferred embodiment was isolated via this procedure, in a yield of 53% by mass.

E. Synthesis of the Third Preferred Embodiment of the Invention

Figure 5:
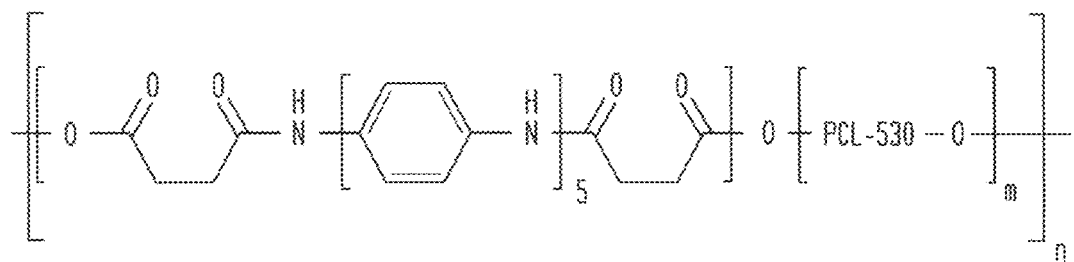
FIG. 5 shows the structure of a third preferred embodiment of the invention, using PCL-530.
Figure 6:
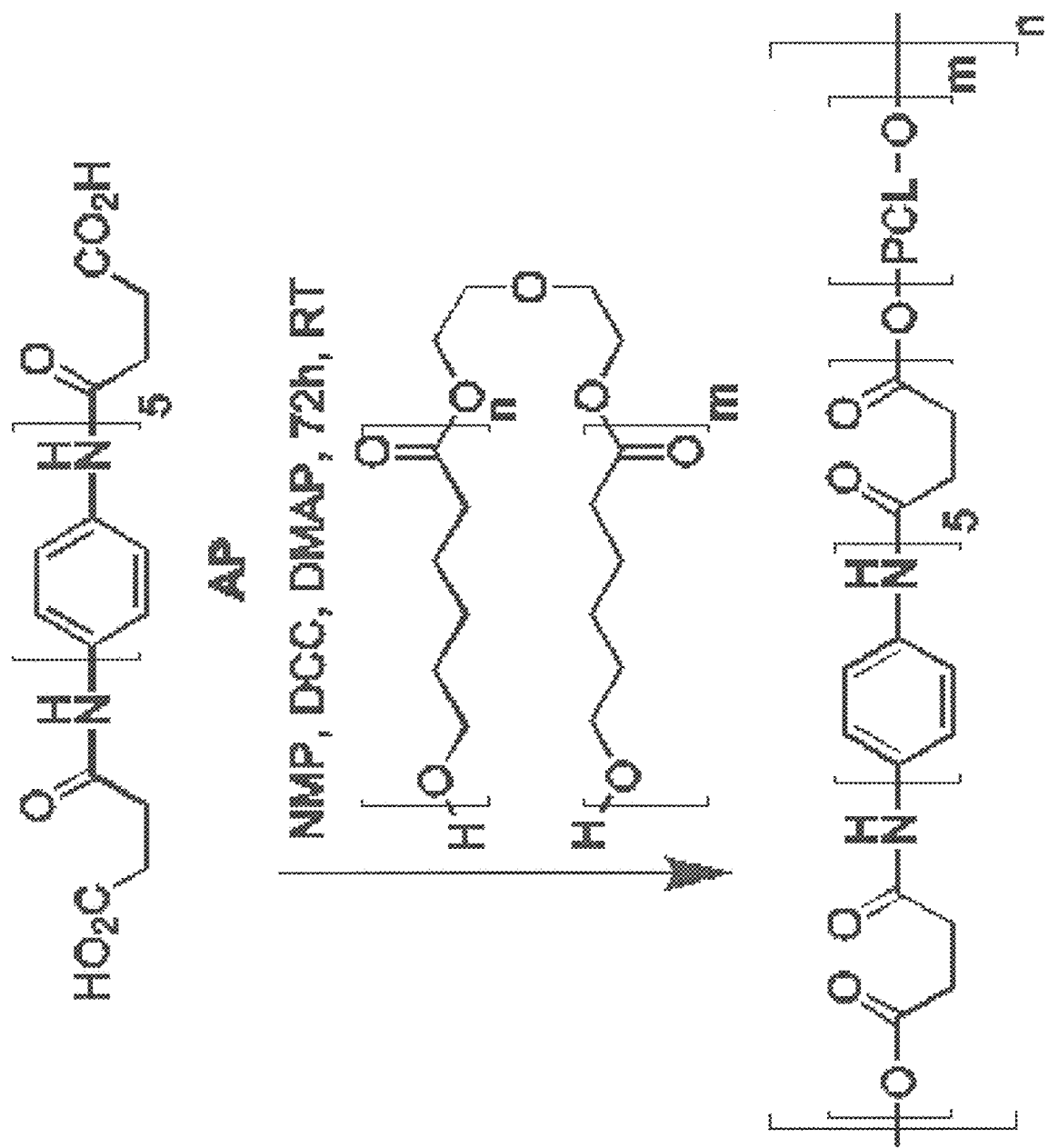
FIG. 6 shows the synthesis of the third and fourth preferred embodiments of the invention.

The third preferred embodiment of the invention (FIG. 5) was synthesized using the synthesis illustrated in FIG. 6, using poly(caprolactone) diol with an average molecular weight of 530 Da. 2.2 g of the third preferred embodiment was isolated via this procedure, in a yield of 62% by mass.

F. Synthesis of the Fourth Preferred Embodiment of the Invention

Figure 7:
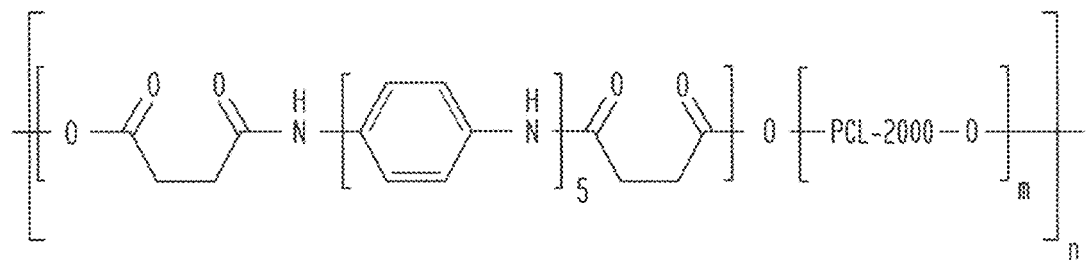
FIG. 7 shows the structure of a fourth preferred embodiment of the invention, using PCL-2000.

The fourth preferred embodiment of the invention (FIG. 7) was synthesized using the same synthesis used for the third preferred embodiment, except that poly(caprolactone) diol with an average molecular weight of 2,000 Da. was employed. 1.0 g of the fourth preferred embodiment was isolated via this procedure, in a yield of 25% by mass.

G. Doping of the Preferred Embodiments and Drug Delivery

Figure 8:
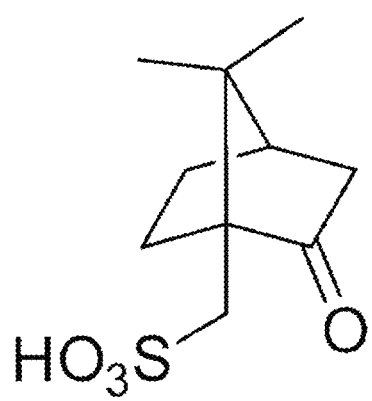
FIG. 8 shows the structure of camphorsulfonic acid.
Figure 9:
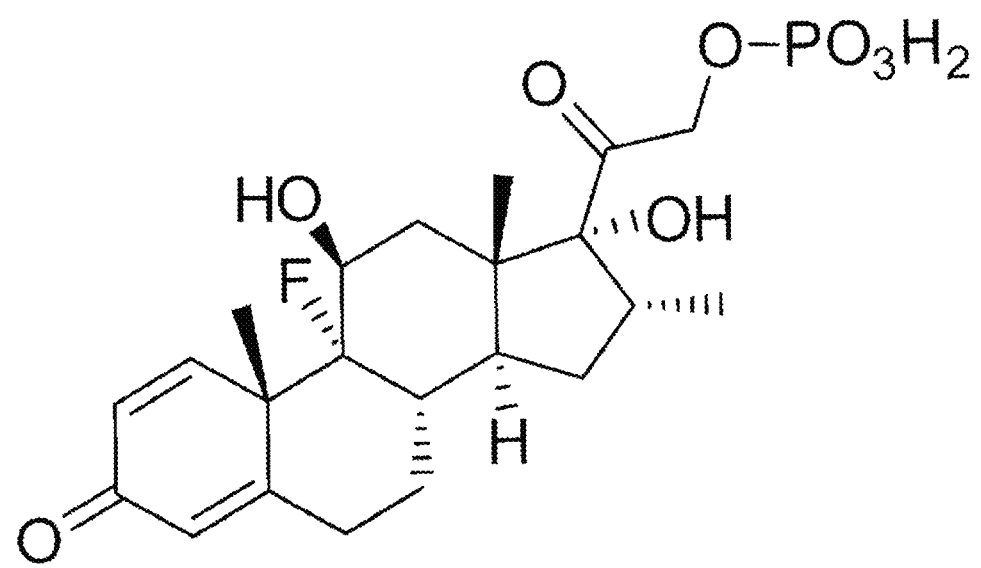
FIG. 9 shows the structure of dexamethasone phosphate.

Advantageously, electroactive materials in accordance with the invention can be doped. One suitable dopant is camphorsulfonic acid (FIG. 8), which can promote adhesion of e.g. C6 cells, keratinocytes, MC3T3-E1 cells, osteoblasts, PC12 cells, Schwann cells, human Mesenchymal stem cells, human dermal fibroblasts and potentially others. Alternatively, the dopant can be the drug to be delivered to the living subject. Where for example it is necessary to treat inflammation, the dopant can be dexamethasone phosphate (FIG. 9), which has anti-inflammatory properties.

The ability of electroactive materials in accordance with the invention to deliver a drug to a living subject was demonstrated using dexamethasone phosphate (DMP), an anti-inflammatory having a molecular weight of 490 Da. Release of DMP into phosphate buffered saline (PBS) solution was monitored using UV spectroscopy. Films composed of each of the first, second, third, and fourth preferred embodiments and approximately 3 to 4 mg DMP were prepared on bioinert conductive and non-conductive substrates (glassy carbon electrodes and glass, respectively). DMP loadings were at a mole ratio of 1:1 dexamethasone phosphate: aniline pentamers (approximately 31 wt % for the first and third preferred embodiments and approximately 16 wt % for the second and fourth preferred embodiment). The experimental setups are depicted in FIGS. 10 and 11. The setup depicted in FIG. 10A (using films deposited on glassy carbon substrates) is akin to that used for electrodes implanted for stimulation of the central nervous system in which the tissue surrounding the implant is used as a counter electrode. The setup depicted in FIG. 11A (using films deposited on glass substrates) is a simple closed circuit similar to those proposed to power some conductive tissue scaffolds.

Pulsatile release of DMP from films deposited on glassy carbon substrates was studied by chronoamperometry using 1 minute of electrical stimulation followed by 14 minutes of rest (FIG. 10B) after which the quantity of DMP in the PBS solution was quantified by UV spectroscopy. The medium was unchanged between cycles. The data are reported as cumulative release as a percentage of the total mass of drug in the film and compared to DMP release from unstimulated films. Voltammetry scans and chronoamperometry pulses were always initiated at the open circuit potential of the system. Potential cycling was carried out between 0.7 V and −0.5 V, first sweeping in the positive direction of the potential scale at 50 mV s$^{-1}$.

Passive release of DMP from unstimulated films was low over the course of the experiment (1.5 hours), approximately 8% for the first preferred embodiment, approximately 3% for the second preferred embodiment, and approximately 2% for the third and fourth preferred embodiments (FIG. 10C). Over a period of 24 days this increased to approximately 83% for the first and second preferred embodiments, approximately 48% for the third preferred embodiment, and approximately 35% for the fourth preferred embodiment. In contrast, electrochemically-triggered release of the drugs by potential cycling (FIG. 10C) resulted in the release of approximately 20 to 65% of the drug during the initial cycle. Subsequent cycles were observed to release 5 to 10% per cycle for the first six cycles, after which the majority of the drug had been released from all of the films.

The electrochemically-triggered release of DMP from films deposited on glass substrates (FIG. 11A) was studied. A potential step of +0.6 V was applied to each film for 30 seconds, followed by 29.5 minutes of rest (FIG. 11B) after which the quantity of DMP in solution was quantified by UV spectroscopy. The first stimulation released 5 to 25% of the drug from the films (FIG. 10C), the first and second stimulation released 25 to 50%, and the third stimulation released between 50 to 90% of the drugs from the films, all of which are clearly distinguishable from the passive release profiles.

H. Biodegradability

To demonstrate the susceptibility of the materials in accordance with the invention to hydrolytic degradation in vitro, films of each of the preferred embodiments were incubated in PBS in the absence or presence of cholesterol esterase (4 units/mL) which is an enzyme known to hydrolyze ester bonds in polyesters. The mass of each film was observed to decrease very slowly over a week, and the presence of the esterase moderately increased the rate at which this occurs. It was consequently concluded that the films would degrade slowly if administered in vivo (over the period of weeks to months). Analogous CSA-doped materials have been shown to support the adhesion of a variety of cells including C6 cells, keratinocytes, MC3T3-E1 cells, osteoblasts, PC12 cells and Schwann cells, human Mesenchymal stem cells, and human dermal fibroblasts. Films of the first and third preferred embodiments were found to be prone to fracture as a consequence of exposure to dynamic shear forces encountered during multiple media changes at 37° C. Films of the second and fourth preferred embodiments were much more robust and both human dermal fibroblasts and human mesenchymal stem cells were seen adhered to the films, suggesting their potential for in vivo implantation for a variety of applications (e.g., drug eluting coatings on completely biodegradable implants).

Electrically triggered drug release from materials in accordance with the invention provides a novel platform for drug delivery. Synthesis and purification of polymers in accordance with the preferred embodiments is simple and scalable, requiring only 3 steps from commercially available starting materials. Polymers in accordance with the preferred embodiments are solution processable, thus facilitating the preparation of materials with a high drug loading of 16 or 31 wt %. Although DMP was used as a clinically applied model drug, this was only for purposes of illustration and other biologically-active molecules could be delivered instead, using the stimulation paradigms described here or others. Persons of ordinary skill in the art could modulate the release profiles of these molecules via simple modifications of the electrical input. Materials in accordance with the invention have potential to be used for the manufacture of completely biodegradable drug delivery systems.

If non-polymeric electrochemically responsive units are used instead of polymers, those units will not necessarily display two alcohol functional groups. Rather, other units could be substituted for diols. As long as those other units are capable of being chemically bonded to the electrochemically responsive unit (if e.g. the other unit is an aldehyde, the electrochemically responsive unit will be terminated with an oxyamine and the bond will be an oxime bond) they need only be degradable to units that are water soluble and have molecular weights that are below the renal filtration limit.

Although preferred embodiments have been described above, the scope of the invention is limited only by the following claims:

The invention claimed is:
1. A method of delivering a drug to a living patient, comprising: implanting a doped biodegradable electroactive polymer in the patient; and stimulating the doped polymer by application of an electrical potential to the polymer,
  wherein stimulating the doped polymer causes delivery of the drug to the patient,
  wherein the biodegradable electroactive polymer including a water soluble electrochemically responsive unit linked to another unit by a biodegradable bond, and the drug, wherein the biodegradable electroactive polymer is of the form:

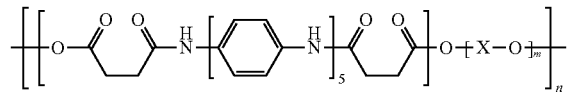

wherein X is polyethylene glycol or polycaprolactone.

2. The method of claim 1, wherein each of the units has a molecular weight less than the renal filtration threshold.

3. The method of claim 1, wherein X is:
poly(ethylene glycol)s having average molecular weight of 400 Da.; or
poly(ethylene glycol)s having average molecular weight of 2000 Da.

4. The method of claim 1, wherein X is:
poly(caprolactone)s having average molecular weight of 530 Da.; or
poly(caprolactone)s having average molecular weight of 2000 Da.

5. The method of claim 1, wherein the drug is dexamethasone phosphate.

* * * * *